(12) United States Patent
Toh

(10) Patent No.: US 6,585,724 B2
(45) Date of Patent: Jul. 1, 2003

(54) OPHTHALMIC SURGERY APPARATUS

(75) Inventor: Minoru Toh, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/820,971

(22) Filed: Mar. 30, 2001

(65) Prior Publication Data

US 2002/0026179 A1 Feb. 28, 2002

(30) Foreign Application Priority Data

Mar. 31, 2000 (JP) ........................................ 2000-098411

(51) Int. Cl.$^7$ ................................................ A61B 18/18
(52) U.S. Cl. .................................. 606/5; 606/4; 606/10; 606/11; 606/12; 351/208; 351/209; 351/211; 351/221
(58) Field of Search ........................... 606/4–6, 10–13, 606/17; 351/208–211, 221

(56) References Cited

U.S. PATENT DOCUMENTS

| | | | | |
|---|---|---|---|---|
| 3,724,932 A | * | 4/1973 | Cornsweet et al. ............ | 351/7 |
| 5,507,799 A | | 4/1996 | Sumiya | |
| 5,562,656 A | | 10/1996 | Sumiya | |
| 5,637,109 A | | 6/1997 | Sumiya | |
| 6,030,376 A | * | 2/2000 | Arashima et al. .............. | 606/4 |
| 6,159,202 A | * | 12/2000 | Sumiya et al. ................. | 606/4 |
| 6,257,722 B1 | * | 7/2001 | Toh ............................. | 351/208 |

FOREIGN PATENT DOCUMENTS

| | | |
|---|---|---|
| GB | 2170910 A | 8/1986 |
| JP | 07-303609 | 11/1995 |
| JP | 09-038037 | 2/1997 |

OTHER PUBLICATIONS

D. H. Bahi et al. "Use of a Discrete Electro–Oculographic Control System With and Without Oscillatory Motion of the Head." Proceedings of the 1991 IEEE 17 th Annual Northeast Bioengineering Conference, vol. Conf. 17, Apr. 4, 1991, pp 129–130.*

* cited by examiner

Primary Examiner—Linda C. M. Dvorak
Assistant Examiner—Ahmed Farah
(74) Attorney, Agent, or Firm—Finnegan, Henderson, Farabow, Garrett & Dunner LLP

(57) ABSTRACT

An ophthalmic surgery apparatus by which treatment laser beam is irradiated onto a desired portion of a patient's eye and for treatment of the portion, the apparatus includes: a laser irradiating unit having a laser beam source which emits the treatment laser beam, and an irradiating optical system which optically guides the treatment laser beam emitted from the laser beam source onto the portion; an ocular movement detecting unit which detects a potential difference between a cornea and a retina, and detects an ocular movement of the patient's eye based on the detected potential difference; and an irradiation controlling unit which controls the irradiating unit based on a result of detection by the detecting unit.

8 Claims, 7 Drawing Sheets

OPHTHALMIC SURGERY APPARATUS

BACKGROUND OF THE INVENTION

The present invention relates to an ophthalmic surgery apparatus for performing treatment by irradiating a treatment laser beam to a subject's eye, and more particularly to a mechanism for aligning the irradiation optical axis of a laser irradiating optical system for applying a treatment laser beam, with a patient's eye, and also to a laser irradiation controlling mechanism associated with the alignment.

As an ophthalmic surgery apparatus for performing treatment by irradiating a laser beam for treatment to a patient's eye, a corneal surgery apparatus using an excimer laser beam, for example, is known. This apparatus is used for refractive correction by changing the curvature of the cornea with an excimer laser beam irradiated to the corneal surface.

In this apparatus, the patient is caused to gaze at a fixation target to fix the position of the patient's eyeball, and the irradiation optical axis of the laser irradiating optical system and the patient's eye are brought into alignment in a desired state by using an alignment target or the like. After completion of the alignment, a part of the cornea is ablated at a set amount within an intended area.

As disclosed in U.S. Pat. No. 6,159,202, a corneal surgery apparatus (ophthalmic surgery apparatus) having an automatic tracking mechanism has also been proposed. This apparatus has a function of moving the irradiation optical axis of the laser irradiating optical system to follow (track) the movement of the patient's eyeball. This apparatus makes it possible to prevent the cornea from being ablated in an unplanned shape as the operator continues the laser irradiation without becoming aware of the movement of the patient's eyeball during the laser irradiation. With this tracking mechanism, an image of an anterior portion of the patient's eye is constantly obtained by a CCD camera or the like during the laser irradiation. Then, if it is detected on the basis of the obtained image that the detected position of the pupillary center is moved out of a predetermined first allowable range from a reference position, such as irradiation optical axis, (e.g., out of a range of 0.005 mm in radius from the reference position), the irradiation optical axis is subjected to tracking so that the position of the pupillary center and the reference position will be aligned with each other on the basis of the obtained image. In addition, the laser irradiation is discontinued if the position of the pupillary center is moved out of a predetermined second allowable range, such as the imaging range of the camera, the movable range of the irradiation optical axis, and a range offset largely from the reference position (e.g., a range of 1 mm in radius from the reference position).

However, the processing speed associated with image capture by the camera and image process is low as compared to the speed of the eyeball movement. For this reason, the automatic tracking in the related art has a slight time lag until the irradiation optical axis is subjected to tracking or the laser irradiation is discontinued after the patient's eye is moved. Particularly, in a case where the laser irradiation is discontinued, an unexpected portion may be ablated during the time lag until the discontinuance.

SUMMARY OF THE INVENTION

In view of the above-described problems of the related art, an object of the invention is to provide an ophthalmic surgery apparatus capable of performing accurate treatment by ensuring appropriate alignment between the irradiation optical axis of the laser irradiating optical system and the patient's eye.

(1) An ophthalmic surgery apparatus by which treatment laser beam is irradiated onto a desired portion of a patient's eye and for treatment of the portion, the apparatus comprising:
   a laser irradiating unit having a laser beam source which emits the treatment laser beam, and an irradiating optical system which optically guides the treatment laser beam emitted from the laser beam source onto the portion;
   an ocular movement detecting unit which detects a potential difference between a cornea and a retina, and detects an ocular movement of the patient's eye based on the detected potential difference; and
   an irradiation controlling unit which controls the irradiating unit based on a result of detection by the detecting unit.

(2) The apparatus of (1), wherein the detecting unit includes a plurality of electrodes to be attached to a periphery around the patient's eye.

(3) The apparatus of (2), wherein the electrodes includes a pair of electrodes to be attached to the periphery around the patient's eye and located in at least one of vertical and horizontal directions.

(4) The apparatus of (1), wherein irradiation controlling unit controls the irradiating unit so that the laser irradiation is discontinued if the detecting unit detects a potential difference not smaller than or not larger than a predetermined threshold value.

(5) The apparatus of (1), further comprising:
   a setting unit which variably sets the threshold value based on inputted data of the patient's eye.

(6) The apparatus of (1), further comprising:
   a moving unit which relatively moves an irradiation optical axis of the irradiating optical system with respect to the patient's eye; and
   a movement controlling unit which controls the moving unit based on a result of detection by the detecting unit.

(7) The apparatus of (6), further comprising:
   a signal generating unit which generates a tracking signal for tracking the movement of the patient's eye if the detection unit detects a potential difference not smaller than or not larger than a predetermined threshold value, and
   wherein the movement controlling unit controls the moving unit based on the tracking signal.

(8) The apparatus of (1), wherein:
   the apparatus includes a corneal surgery apparatus; and
   the laser beam source emits excimer laser beam as the treatment laser.

(9) An ophthalmic surgery apparatus by which treatment laser beam is irradiated onto a desired portion of a patient's eye and for treatment of the portion, the apparatus comprising:
   a laser irradiating unit having a laser beam source which emits the treatment laser beam, and an irradiating optical system which optically guides the treatment laser beam emitted from the laser beam source onto the portion;
   an ocular movement detecting unit which detects a potential difference between a cornea and a retina, and detects an ocular movement of the patient's eye based on the detected potential difference;
   a moving unit which relatively moves an irradiation optical axis of the irradiating optical system with respect to the patient's eye; and a movement controlling unit which controls the moving unit based on a result of detection by the detecting unit.

(10) The apparatus of (9), further comprising:
a signal generating unit which generates a tracking signal for tracking the movement of the patient's eye if the detection unit detects a potential difference not smaller than or not larger than a predetermined threshold value, and
wherein the movement controlling unit controls the moving unit based on the tracking signal.

The present disclosure relates to the subject matter contained in Japanese patent application No. 2000-98411 (filed on Mar. 31, 2000), which is expressly incorporated herein by reference in its entirety.

DESCRIPTION OF THE PREFERRED EMBODIMENT

Figure 1:
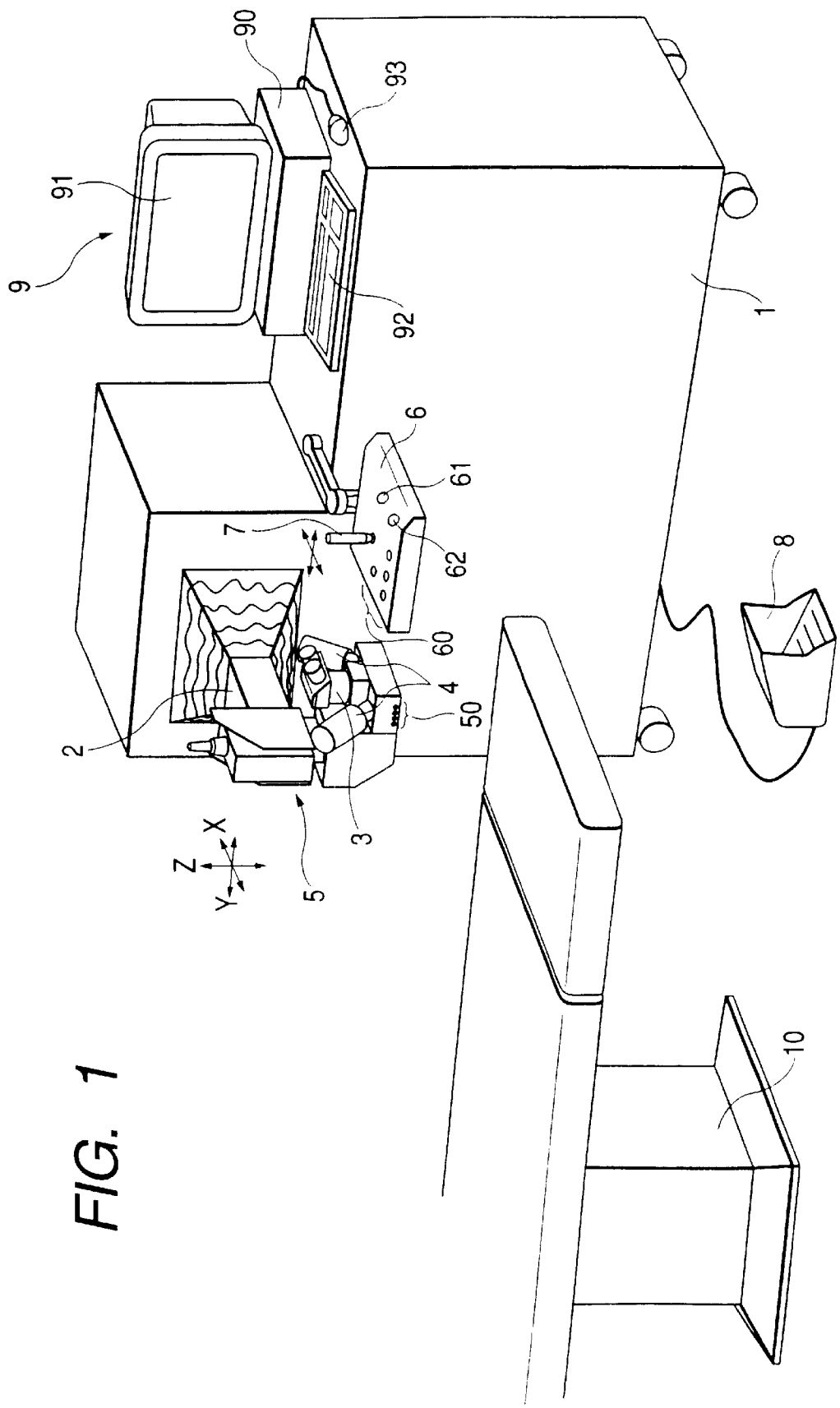
FIG. 1 is an overall schematic diagram of a corneal surgery apparatus in accordance with an embodiment of the invention.

Referring now to the drawings, a description will be given of an embodiment of the invention.

[Overall Construction]

Figure 2:
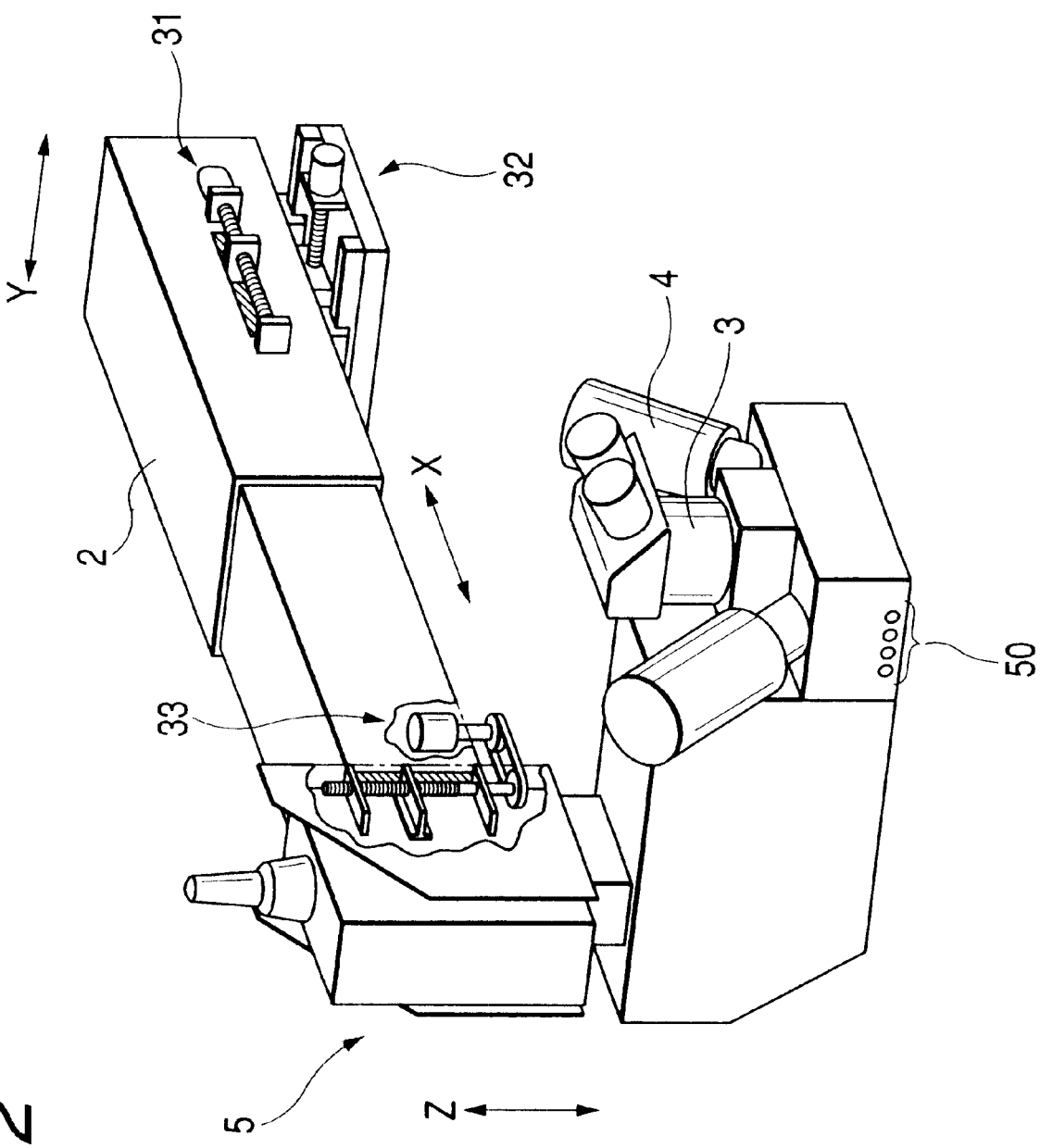
FIG. 2 is a diagram illustrating moving mechanisms for moving an arm portion and an arm distal end portion of the apparatus.

FIG. 1 is an overall schematic diagram of a corneal surgery apparatus for performing corneal surgery using an excimer laser beam. Reference numeral 1 denotes a main body of the apparatus, in which an excimer laser light source and the like are incorporated. Numeral 2 denotes an arm portion for guiding an excimer laser beam from the main body 1 to an arm distal end portion 5 having a laser irradiating port. The distal end portion 5 is further provided with an observing optical system including a binocular microscope unit 3 and an illuminating unit 4, an eyeball-position detecting optical system (which systems will be described later in detail), and the like. The arm portion 2 is moved in an X-direction (in a left-and-right direction with respect to the operator) by an X-direction arm driving device 31, and is moved in a Y-direction (in a back-and-forth direction with respect to the operator) by a Y-direction arm driving device 32. Further, the distal end portion 5 is moved in a Z-direction by a Z-direction arm driving device 33. Each of the arm driving devices has a known arrangement including a motor, a slide mechanism, and the like (see FIG. 2).

Reference numeral 6 denotes a controller, which has a joystick 7 for imparting signals for driving the arm portion 2 in the X- and Y-directions, various operating switches, and the like. Various signals from the controller 6 are sent to an arithmetic control unit 30 which will be described later. Numeral 8 denotes a foot switch for sending a trigger signal for instructing laser emission to the arithmetic control unit 30. Numeral 9 denotes a computer for effecting the input of various data on necessary surgical conditions, calculation of surgical data (laser irradiation data), display, storage, and the like, and is comprised of a main unit 90, a monitor 91, a keyboard 92, a mouse 93, and the like. Numeral 10 denotes a bed for the patient to lie.

Reference numeral 50 denotes a connector for connecting cords of electrodes attached to the periphery of the patient's eye, and in this embodiment four connectors are provided (a detailed description thereof will be given later).

[Construction of Various Units]

Figure 3:
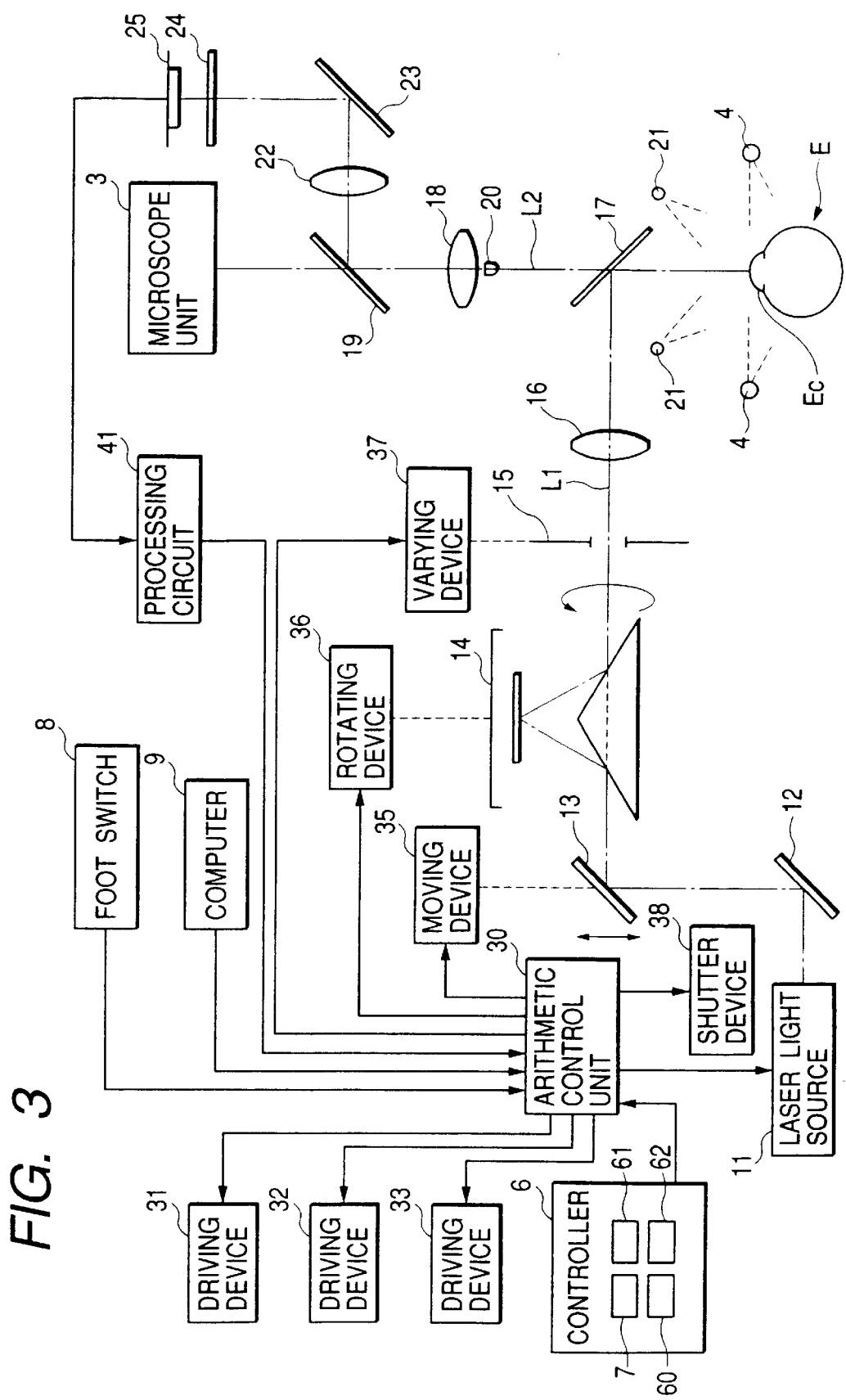
FIG. 3 is a schematic diagram of an optical system and a control system of the apparatus.

FIG. 3 is a schematic diagram of the optical system and the control system of this apparatus.

<Laser Irradiating Optical System>

Reference numeral 11 denotes a laser light source for emitting an excimer laser beam (hereafter simply referred to as the laser beam) with the wavelength of 193 nm. The laser beam emitted from the laser light source 11 and having a rectangular cross section is reflected by plane mirrors 12 and 13. The mirror 13 is moved in parallel by a moving device 35, whereby the laser beam is moved to cover the entire region of the opening of an aperture 15. Numeral 14 denotes an image rotator, which is rotated by a rotating device 36 to rotate the laser beam reflected by the mirror 13 about the irradiation optical axis L1. Numeral 15 denotes the aperture for limiting the irradiating region of the laser beam, and its aperture diameter is changed by a varying device 37. Numeral 16 denotes a projecting lens for projecting the image of the aperture 15 onto the cornea Ec of the patient's eye E. The aperture 15 is located at a conjugated position of the cornea Ec with respect to the lens 16, so that a region to be ablated is limited as the region defined by the aperture 15 is projected onto the cornea Ec. It should be noted that since such an optical system is described in U.S. Pat. Nos. 5,507,799, 5,637,109 and the like, reference should be made to them.

Reference numeral 17 denotes a dichroic mirror which has the characteristic of reflecting the excimer laser beam, and transmitting the visible light and the infrared light, and by which the irradiation optical axis L1 of the laser irradiating optical system is made coincident with the detection optical axis L2 of an objective lens 18 of the observing optical system and the eyeball-position detecting optical system which will be described later.

<Observing Optical System>

Reference numeral 18 denotes the objective lens, and numeral 19 denotes a dichroic mirror having the characteristic of transmitting the visible light and reflecting the infrared light. The bundle of rays of an image of an anterior portion of the eye E illuminated by the visible illuminating light from the illuminating unit 4 is made incident on the microscope unit 3 through the dichroic mirror 17, the lens 18, and the dichroic mirror 19. Consequently, the operator is able to observe the eye E through the binocular microscope unit 3. It should be noted that an unillustrated reticle plate is inserted in the observing optical system, which can be used as a reference for alignment of the eye E in the X- and Y-axis directions.

A target projecting optical system (refer to U.S. Pat. No. 5,562,656) comprising two slits is disposed in the observing optical system so as to effect alignment in the Z-axis direction. Numeral 20 denotes a fixation lamp placed on the detection optical axis L2.

<Eyeball-Position Detecting Optical System>

Reference numeral 21 denotes an infrared illuminating light source such as an LED, and four infrared illuminating light sources 21 are arranged at 90-degree intervals with the irradiation optical axis L1 (the detection optical axis L2) as the center. Numeral 22 denotes an imaging lens; 23, a reflecting mirror; 24, an infrared transmitting filter; and 25, a CCD camera for infrared light.

The bundle of rays of an image of an anterior portion of the eye E illuminated by the infrared illuminating light is passed through the dichroic mirror 17 and the lens 18 and reflected by the dichroic mirror 19. Subsequently, the image is formed on the imaging plane of the camera 25 by the lens 22 through the mirror 23 and the filter 24. At this time, the filter 24 cuts off the visible light which is slightly reflected by the dichroic mirror 19.

<Control System>

Reference numeral 30 denotes the arithmetic control unit for controlling the drive of the laser light source 11, the moving device 35, the rotating device 36, the varying device 37, a shutter device 38 to be described later, the arm driving devices 31, 32, and 33, and the like.

<Ocular-Movement Detecting System>

Figure 4:
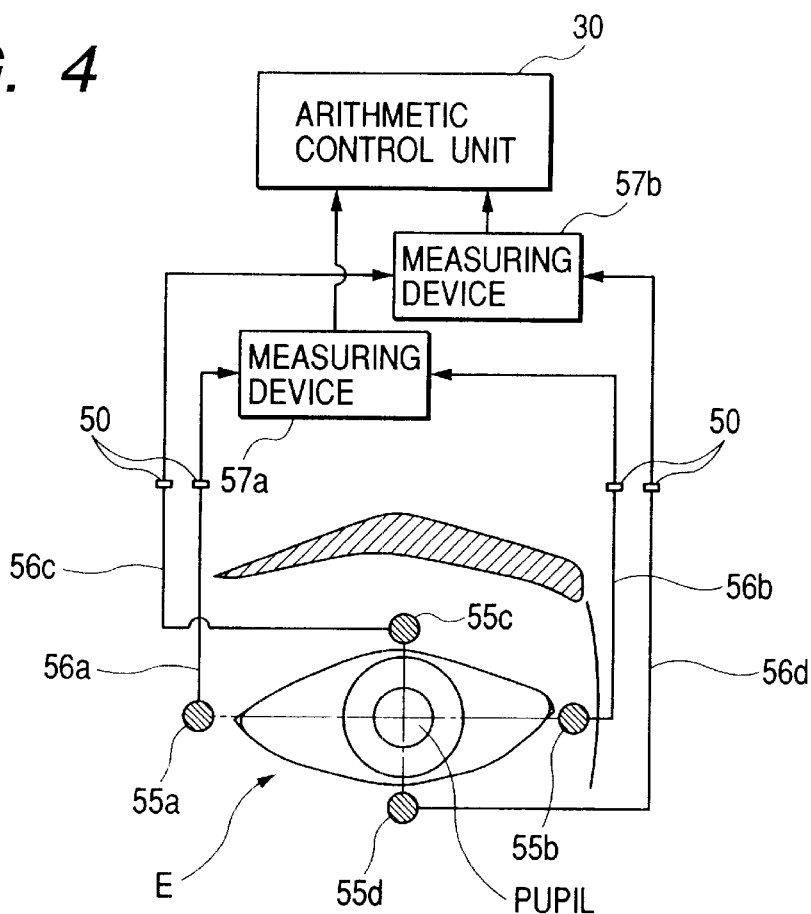
FIG. 4 is a schematic diagram of an ocular-movement detecting system of the apparatus.

FIG. 4 is a schematic diagram of the ocular-movement detecting system of this apparatus. In an organism, very weak electricity is generated in any part of its body. This is applied also to the eyeball, and the cornea side has plus (+) potential, while the retina side has negative (−) potential (this is called the resting potential of the eyeball) as if a small battery is disposed within the eyeball. When the eyeball moves (rotates), a change of voltage distribution occurs in the surrounding electric field due to this resting potential, and if this change is grasped using electrodes, the ocular movement can be detected as an electrical change (this is called the electro-oculography). Accordingly, in this apparatus, the alignment between the irradiation optical axis L1 and the position of the eye E and the control of laser irradiation linking with the alignment are effected on the basis of the electrical change caused due to the ocular movement.

Reference numerals 55a to 55d denote electrodes, which are attached to the periphery of the eye E using electrode glue or vinyl tape. The electrodes are attached at locations on the orbital margin (orbital rim) and on horizontal and vertical lines which are passed through the pupil of the eye viewing forwardly. It should be noted that there are various types of the electrodes, but in this embodiment silver-tray electrodes for electroencephalogram are used.

Reference numerals 57a and 57b denote measuring devices. The electrodes 55a and 55b for obtaining the horizontal movement of the eyeball are connected to the measuring device 57a via respective cords 56a and 56b and connectors 50, so that the measuring device 57a measures the change in eye position in the horizontal direction as a potential difference. The electrodes 55c and 55d for obtaining the vertical movement of the eyeball are connected to the measuring device 57b via respective cords 56c and 56d and connectors 50, so that the measuring device 57b measures the change in eye position in the vertical direction as a potential difference. It should be noted that the measuring devices 57a and 57b are each provided with a high-cut filter for fetching only the desired electric activity (excluding an electromyogram and the like ascribable to the orbicularis oculi muscle of the eye and the like), an amplifier for amplifying the very weak electric potential (about 1 mV or thereabouts, and approximately equivalent to that of an electrocardiogram) accompanying the ocular movement, a calibrator, a processing circuit to be described later, and so on.

[Detection of the Position of the Eyeball]

Figure 5:
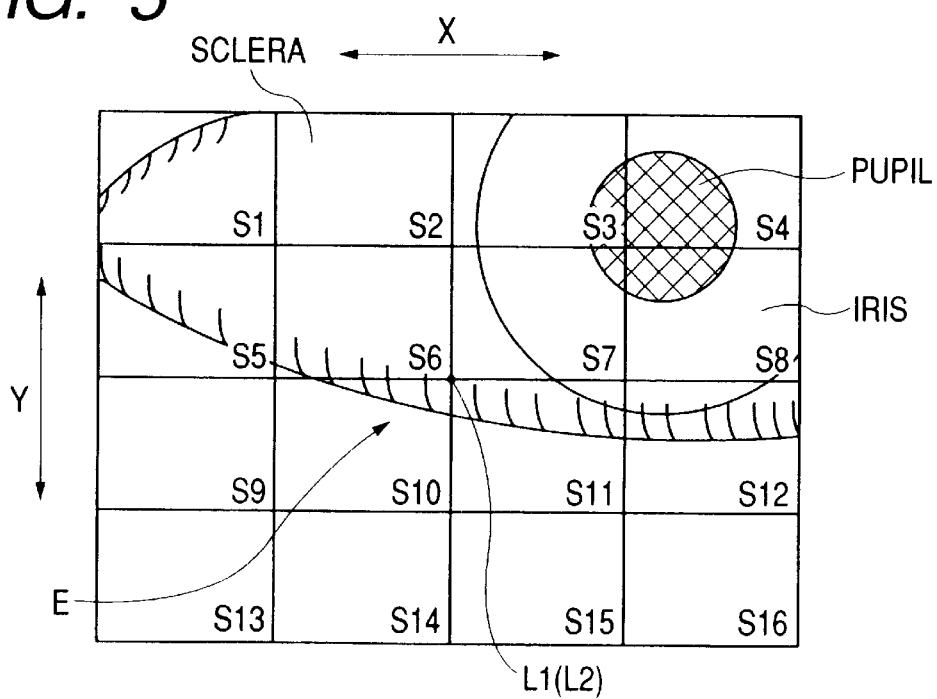
FIG. 5 is a diagram illustrating an example in which an image centering on the irradiation optical axis is divided into 16 areas.
Figure 6:
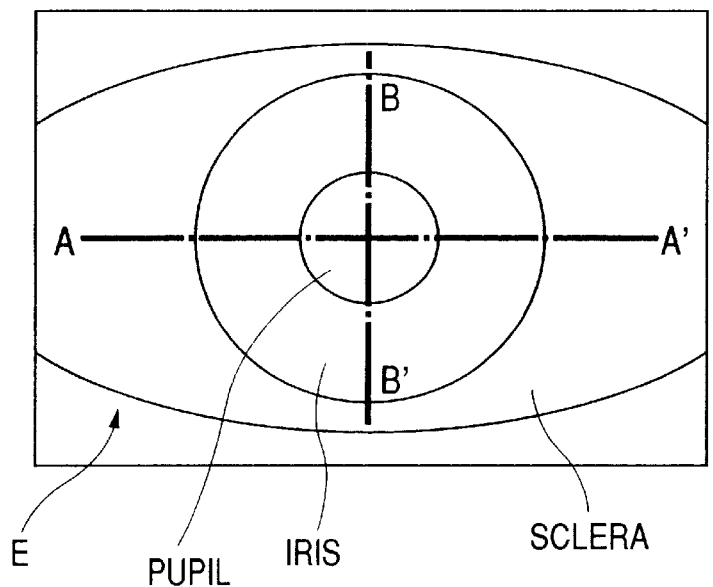
FIG. 6 is a diagram illustrating an image of the anterior portion of the patient's eye picked up by a CCD camera.
Figure 7:
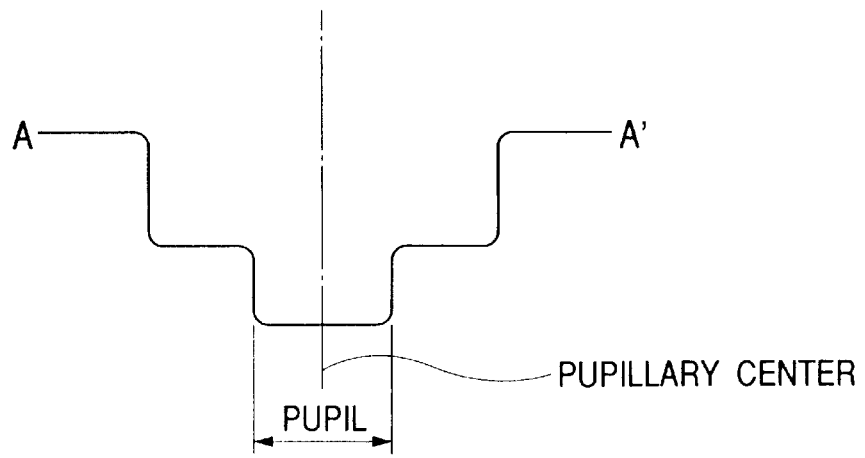
FIG. 7 is a diagram illustrating the distribution of the quantity of light on a line A–A' in FIG. 6.

Next, a description will be given of a method of detecting the position of the eyeball using the camera 25. It should be noted that, in this embodiment, since an object with which the irradiation optical axis L1 is aligned is set as the position of the pupillary center, a description will be given of the detection of the position of the pupillary center. FIG. 5 is a diagram illustrating an example in which an obtained image centering on the irradiation optical axis L1 (the detection optical axis L2) is divided into 16 areas. FIG. 6 is a diagram illustrating an image of an anterior portion of the eye E, obtained by the camera 25. FIG. 7 is a diagram illustrating the distribution of the quantity of light on a line A–A' obtained from imaging signals from the camera 25.

First, information on the relative density of reflected light from the anterior portion as a consequence of illumination of the infrared light from the light source 21 is detected. In this detection, as shown in FIG. 5, a two-dimensional image obtained by the camera 25 is processed such that an image centering on the irradiation optical axis L1 (the detection optical axis L2) is divided into 4×4, i.e. 16, areas (S1 to S16). Of pixels (125 pixels×125 pixels) in each area, a predetermined number of pixels (e.g., 64 pixels) subject to the detection of the relative density are preliminarily set in terms of pixel position so that the pixels to be detected are distributed uniformly within the area (all the pixels may be set as the object to be detected, but if a limited number of pixels necessary for detection are set as the object to be detected, the processing speed can be increased). Image signals from the camera 25, after being digitally converted by a processing circuit 41, are subjected to predetermined processing and are inputted to the arithmetic control unit 30. The arithmetic control unit 30 obtains degrees of relative density of each of the pixel sets preliminarily for the respective areas on the basis of the inputted signals. Since the degree of the relative density for each pixel has been digitized, it is possible to obtain values of relative density numerically expressed in, for example, 256 steps including 0 to 255 steps (the 0 side is the darkest, and the 255 side is the brightest).

Next, on the basis of the information on relative density values of the pixels set preliminarily for the respective areas, the arithmetic control unit 30 fetches relative density information of a predetermined range (e.g., 20 steps) using the step of the lowest (the densest) relative density value in the area as a reference. Then, the number of pixels whose density values fall within the predetermined range is counted for each area, and a determination is made as to whether or not the counted number of pixels satisfies a predetermined number (e.g., 20). If the counted number satisfies the predetermined number (20), a determination is made that the pupil (or the iris around the pupil) is located within the area. If the counted number does not satisfy the predetermined number (20), a determination is made that the pupil is located partially within the area or that portions having low relative density values, such as eyelashes, are located in the area, and it is therefore determined that the pupil is not detected.

If there are a plurality of areas which satisfy the predetermined number (20), and if there are areas which are not adjacent to each other, a comparison is made in the counted number of the pixels between the area having the largest number and the area which is not adjacent thereto, and a determination is made as to whether or not there is a predetermined number of discrepancy (e.g., 10). This is because even if the eyelashes or the like are located at a position distant from the pupil, if there is a discrepancy in the counted number of pixels, a determination is made that the pupil is located in the area having the larger number, thereby discriminating that area from that of the eyelashes or the like. If there is no discrepancy of a predetermined number (10), it is determined that the pupil is not detected. If there is a discrepancy of the predetermined number (10), it is specified that the pupil is located in the area having the largest count of pixels. Then, a determination is made as to whether or not the numbers of pixels counted in the four areas, S6, S7, S10, and S11, centering on the irradiation optical axis L1 (detection optical axis L2) are uniform (uniform in a predetermined range). If there is a bias, the irradiation optical axis L1 is moved in the direction in which the bias is overcome on the basis of the position of the area specified as one where the pupil is present. As a result, the pupil can be made close to the irradiation optical axis L1, so that it is possible to detect the substantially entire portion of the pupil (pupillary zone).

It should be noted that, as for the detection of the pupil on the basis of the aforementioned relative density information, the division of the two-dimensional image from the camera 25 into areas may be division into four areas centering on the irradiation optical axis L1 of (detection optical axis L2) for the sake of simplicity.

If the substantially entire portion of the pupil (pupillary zone) has been detected, the position of the pupillary center is detected next. As shown in FIGS. 6 and 7, since the quantity of light differs in the eye depending on the pupil, the iris, and the sclera, so that it is possible to detect the coordinates of the position of the pupillary edge from information on the distribution of the quantity of light. Then, from the coordinates of the position of the pupillary edge, it is possible to obtain the coordinates of the position of its center, i.e., the position of the pupillary center. It should be noted that since the detection of the position of the eyeball is described in U.S. Pat. No. 6,159,202, reference should be made thereto.

[Detection of Ocular Movement (Eyeball Movement)]

Figure 8A:
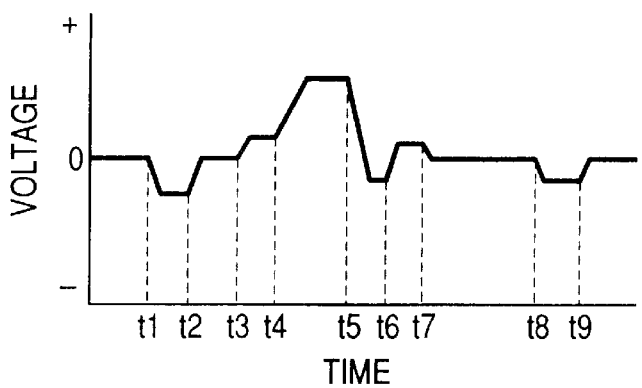
FIG. 8 is a diagram illustrating a method of detecting the ocular movement.
Figure 8B:
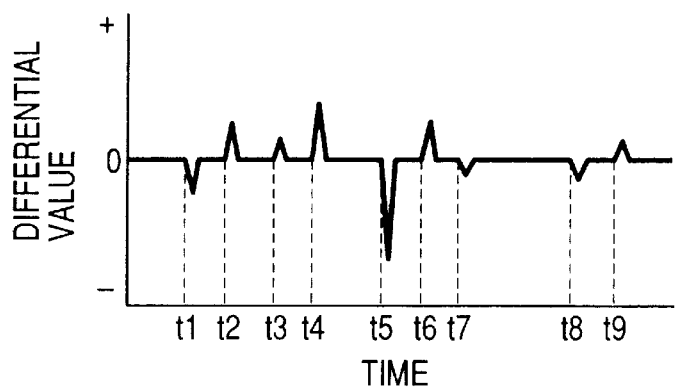
Figure 8C:
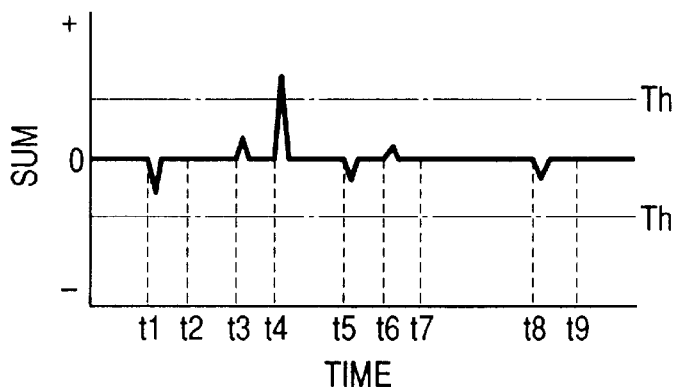
Figure 8D:
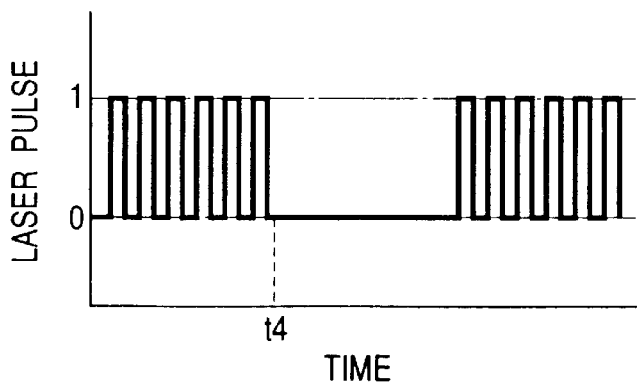

Next, a description will be given of a method of detecting ocular movement. It should be noted that a description will be given herein of only the detection of the ocular movement in the horizontal direction. The potential difference (see FIG. 8A) due to the change in eye position in the horizontal direction, detected by the electrodes 55a and 55b, is fetched and amplified by the measuring device 57a, and is subjected to differentiation processing (see FIG. 8B) by the processing circuit in the measuring device 57a to detect high-speed ocular movement. It should be noted that the potential difference is set to 0 when the eye E is fixed on the fixation lamp 20 in a state in which alignment is obtained between the position of the pupillary center and the reference position (which will be described later) such as the irradiation optical axis L1. Further, the processing circuit in the measuring device 57a chronologically effects summing processing with respect to the potential differences subjected to differentiation processing, and determines whether the sum has reached a level higher (on the plus side) than a predetermined threshold (Th in the drawing) or a level lower (on the minus side) than the same (see FIG. 8C). If the sum has reached a higher level (the plus side) or a lower level (the minus side) relative to the predetermined threshold, a signal to that effect is sent to the arithmetic control unit 30, and the arithmetic control unit 30 discontinues the laser irradiation on the basis of the signal thus sent (see FIG. 8D).

It should be noted that the threshold is set to a value which is at a level higher (on the plus side) or a level lower (on the minus side) than the potential difference at a time when the position of the pupillary center has moved out of the predetermined first allowable range from the reference position (a range which does not require automatic tracking, for example, a range of a radius 0.005 mm from the reference position), and which is at a level lower (on the plus side) or a level higher (on the minus side) than the potential difference at a time when the position of the pupillary center has moved out of the predetermined second allowable range, such as the imaging range of the camera 25, the movable range of the irradiation optical axis L1, and a range largely offset from the reference position (for example, a range of a radius 1 mm from the reference position). Preferably, the threshold is set at a value of the potential difference at a point where misalignment can produce an effect on the result of ablation. Such a threshold may be determined by the main unit 90 of the computer 9 on the basis of the data on the eye E and may be transferred to the arithmetic control unit 30, which in turn sends the threshold to the processing circuits in the measuring devices 57a and 57b so as to be set. In this embodiment, this threshold is set to a potential difference at a point located at a radius of 0.5 mm from the reference position (A range defined by this threshold will be referred to as a third allowable range).

It should be noted that the aforementioned differentiation processing, summing processing, and the like may be effected not by the processing circuits in the measuring devices 57a and 57b but by the arithmetic control unit 30.

[Operation of the Apparatus]

Figure 9:
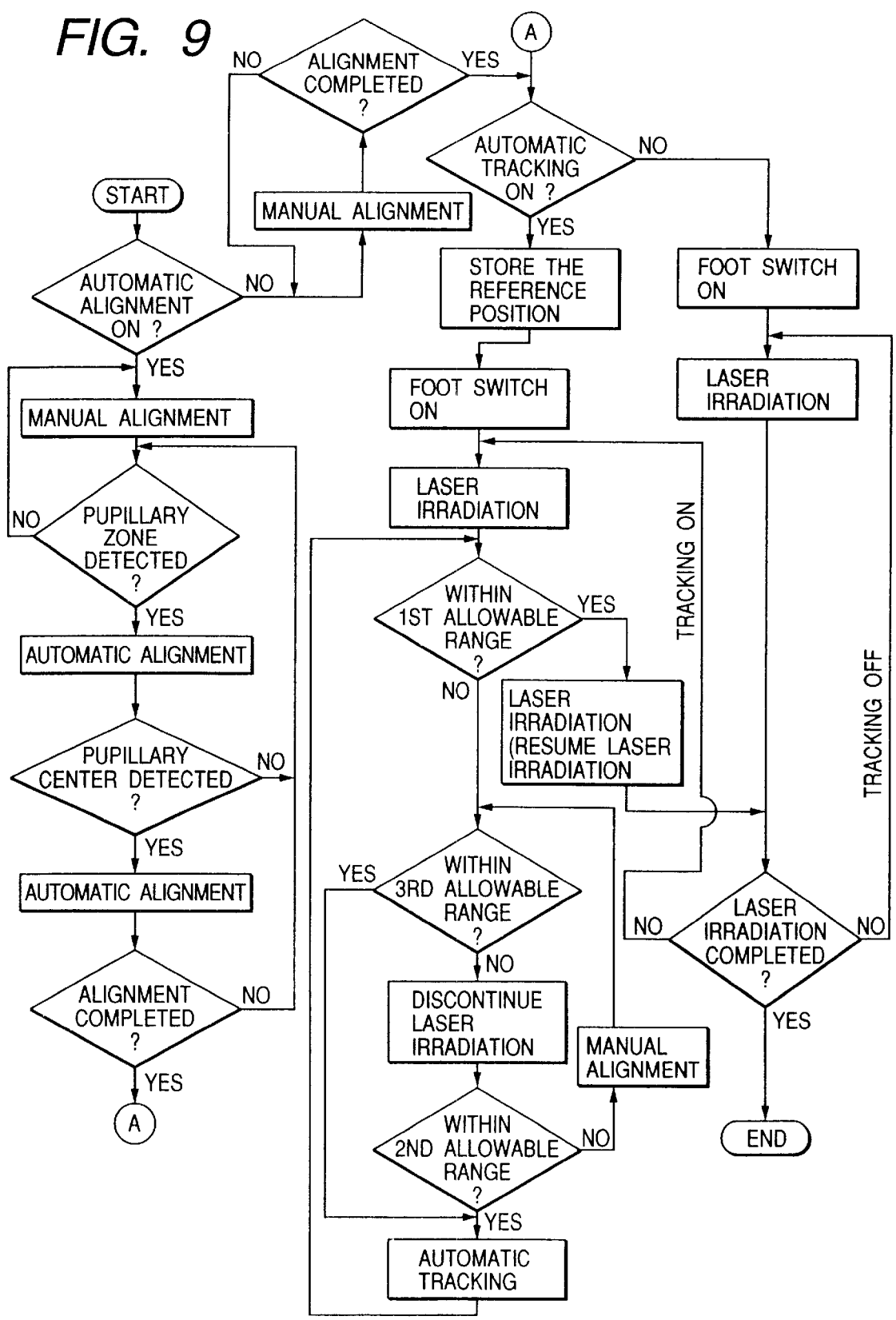
FIG. 9 is a flowchart explaining the operation of automatic alignment and automatic tracking.

In the apparatus having the above-described construction, a description will be given of its operation with reference to the flowchart shown in FIG. 9.

When the power supply of the apparatus is turned on, and the system is started, a menu screen is displayed on the monitor 91 of the computer 9. The corneal surgery using an excimer laser beam includes surgical modes of photorefractive keratectomy (PRK) and phototherapeutic keratectomy (PTK), but in this case PRK is selected on the menu screen. The operator inputs various data such as values of the refractive power examined beforehand, surgical conditions, and the like through the keyboard 92 of the computer 9. The main unit 90 of the computer 9 calculates surgical data such as the amount of corneal ablation and the like on the basis of the inputted data. The calculated surgical data is transferred to the arithmetic control unit 30 by the operation of the keyboard 92 and the mouse 93.

Upon completion of the preparation of inputs, the operator makes the patient lie down on the bed 10, and places the distal end portion 5 provided with the laser irradiation port above the eye E. Then, the operator turns on the respective light sources, and causes the eye E to gaze at the fixation lamp 20.

The operator observes the anterior portion of the eye E illuminated by the illuminating unit 4 using the microscope unit 3, effects alignment in the X- and Y-directions by operating the joystick 7 so that the unillustrated reticle and the pupil have a predetermined relationship, and effects alignment in the Z-axis direction by operating a focus adjusting switch 60. When signals based on the joystick 7 and the switch 60 are inputted to the arithmetic control unit 30, the arithmetic control unit 30 operates (drives) the respective arm driving devices 31, 32, and 33 to move the arm portion 2 in the X- and Y-directions and to move the distal end portion in the Z-direction.

At the time of alignment, if an automatic alignment switch 61 on the controller 6 is set to ON, an automatic alignment mechanism is activated. If the eye E is located within a range in which the pupillary zone and the position of the pupillary center can be detected in the eyeball-position detecting optical system, the apparatus drives the arm driving devices 31 and 32 to move the arm portion 2 in the X- and Y-directions so that the position of the pupillary center and the irradiation optical axis L1 are aligned with each other.

Further, in a case where laser irradiation is effected with the pupillary center and the irradiation optical axis L1 aligned with each other, if a Ready switch 62 on the controller 6 is set to ON, an automatic tracking mechanism is activated. In this case, a predetermined position on the imaging device of the camera 25 (the position of the irradiation optical axis L1 if the automatic alignment is effected) is stored as a reference position, and the tracking of the irradiation optical axis L1 is effected so that the position of the pupillary center is aligned with the reference position (the arm portion 2 is moved in the X- and Y-directions).

The position of the pupillary center obtained by processing the signals from the camera 25 is compared with the reference position, as necessary. Then, when the eye E moves in such a way that the position of the pupillary center moves out of the predetermined first allowable range with respect to the reference position (for example, out of a radius 0.005 mm from the reference position), the arithmetic control unit 30 issues a tracking signal on the basis of the comparison information, and thereby drives the arm driving devices 31 and 32 to move the arm portion 2 in the X- and Y-directions so that the position of the pupillary center comes to be located within the first allowable range with respect to the reference position.

Further, when the eye E moves in such a way that the position of the pupillary center moves out of the predetermined third allowable range with respect to the reference position (for example, out of a radius 0.5 mm from the reference position), since the movement of the eyeball by more than a predetermined level is detected through the electrodes 55a to 55d and the measuring devices 57a and 57b, the arithmetic control unit 30 actuates the shutter device 38 to discontinue the laser irradiation. At this time, if the position of the pupillary center is within the predetermined second allowable range with respect to the reference position (for example, within a radius 1 mm from the reference position), the arithmetic control unit 30 issues a tracking signal on the basis of the comparison information obtained by the camera 25, and drives the arm driving devices 31 and 32 to move the arm portion 2 in the X- and Y-directions so that the position of the pupillary center comes to be located within the first allowable range with respect to the reference position. If the position of the pupillary center is located outside the predetermined second allowable range with respect to the reference position, the position of the pupillary center is made to fall at least within the second allowable range by manual alignment. Consequently, the arithmetic control unit 30 causes the position of the pupillary center to fall within the first allowable range with respect to the reference position using the automatic tracking mechanism.

When the position of the pupillary center has come to be located within the first allowable range with respect to the reference position using the automatic tracking mechanism, the shutter device 38 is actuated again to obtain a state for permitting the laser irradiation. Subsequently, if the operator steps on the foot switch 8, the arithmetic control unit 30 resumes the laser irradiation (see FIG. 8D). The laser beam is applied to the eye E through the irradiating optical system, and the cornea Ec is ablated on the basis of the calculated surgical data.

In a case where the automatic alignment is not used, and automatic tracking is effected in which the position of the irradiation optical axis L1 determined by the manual alignment by the joystick 7 is set as a reference, the irradiation optical axis L1 is positioned at the target position of the eye E by manual alignment. If the switch 62 is turned on upon completion of the alignment, the position of the pupillary center of the eye E at that time is stored as the reference position (i.e., the reference position in this case differs from the irradiation optical axis L1). Then, automatic tracking can be carried out in the same way as in the case of automatic alignment.

It should be noted that the invention is not limited to the above-described embodiment, and various modifications are possible. For example, the invention is also applicable to ophthalmic apparatuses (a laser beam coagulation apparatus etc.) other than the aforementioned corneal surgery apparatus, and can be implemented irrespective of the configurations of their laser irradiating optical systems. In addition, it goes without saying that the invention is applicable to apparatuses which are not provided with the automatic alignment mechanism and the automatic tracking mechanism.

In addition, although in the above-described embodiment the result of detection of the ocular movement is used only for the discontinuance of the laser irradiation, this result may be utilized in the automatic tracking. The arithmetic control unit 30 estimates the direction of movement (rotation) and the amount of movement (rotation) of the eyeball on the basis of the potential difference due to the change of the horizontal position of the eye detected by the electrodes 55a and 55b and the potential difference due to the change of the vertical position of the eye detected by the electrodes 55c and 55d. Then, the arithmetic control unit 30 issues a tracking signal on the basis of the estimation to move the irradiation optical axis L1 in advance. Consequently, tracking can be effected efficiently on the basis of information on the subsequent comparison between the position of the pupillary center based on the camera 25 and the reference position.

In addition, although in the above-described embodiment the irradiation optical axis L1 and the detection optical axis L2 are made coincident with each other, these axes need not be coincident with each other if they have a predetermined positional relationship. It should be noted that, in this case, the realtive position of the irradiation optical axis L1 with respect to the detection optical axis L2 is stored in advance.

In addition, although in the above-described embodiment electrodes and measuring devices for monocular use are prepared for the detection of the ocular movement, electrodes and measuring devices for binocular use may be prepared. In this case, it suffices if the apparatus is provided with an input selection device and a switch for enabling selection between the right eye ocular movement detection and the left eye ocular movement detection. Of course, in this case, a modification may be made in which the number of connectors is increased to eight, for example.

In addition, although in the above-described embodiment control of laser irradiation is effected by the shutter device 38, emission from the laser light source 11 may be controlled.

As described above, in accordance with the invention, alignment between the irradiation optical axis of the laser irradiating optical system and the patient's eye can be made appropriate, thereby making it possible to perform accurate treatment.

What is claimed is:

1. An opthalmic surgery apparatus for treating a desired portion of a patient's eye by irradiating the desired portion with a treatment laser beam, the apparatus comprising:

a laser irradiating unit having a laser beam source which emits the treatment laser beam and an irradiating optical system which optically guides the treatment laser beam emitted from the laser beam source onto the desired portion;

a first ocular movement detecting unit which detects a potential difference of the eye;

an irradiation control unit which controls the laser irradiating unit based on a result of detection by the first ocular movement detecting unit so that irradiation of the treatment laser beam is disabled if the detected potential difference is smaller than a first threshold level on a minus side or larger than a second threshold level on a plus side;

a second ocular movement detecting unit, having a two-dimensional image pickup element for picking up an image of anterior portion of the eye, which detects a predetermined position of the anterior portion by processing the image picked up by the image pickup element;

a moving unit which relatively moves an irradiation position of the treatment laser beam with respect to the eye; and a movement control unit which controls the moving unit based on a result of detection by the second ocular movement detecting unit so that the irradiation position is moved if the detected position is located out of a first allowable range with respect to a reference position, wherein the irradiation control unit controls the irradiating unit based on the result of detection by the second ocular movement detecting unit so that the irradiation of the treatment laser beam is enabled if the detected position is located within a second allowable range with respect to the reference position.

2. The apparatus of claim 1, wherein the first ocular movement detecting unit includes at least one pair of electrodes adapted to be attached to a periphery around the patient's eye and located in at least one of vertical and horizontal directions.

3. The apparatus of claim 2, wherein the electrodes include two pairs of electrodes adapted to be attached to the periphery around the patient's eye and located in the vertical and horizontal directions.

4. The apparatus of claim 1, further comprising:

a setting unit which variably sets at least one of the first and second threshold levels based on inputted data of the patient's eye.

5. The apparatus of claim 1, wherein:

the apparatus includes a corneal surgery apparatus; and the laser beam source emits excimer laser beam as the treatment laser beam.

6. The apparatus of claim 1, wherein the movement control unit controls the moving unit based on the result of detection by the first ocular movement detecting unit.

7. An ophthalmic surgery apparatus for treating a desired portion of a patient's eye by irradiating the portion with a treatment laser beam, the apparatus comprising:

laser irradiating means having a laser beam source which emits the treatment laser beam, and an irradiating optical system which optically guides the treatment laser beam emitted from the laser beam source onto the portion;

first ocular movement detecting means for detecting a potential difference of the eye;

irradiation control means for controlling the irradiating means based on a result of detection by the first ocular movement detecting means so that irradiation of the treatment laser beam is disabled if the detected potential difference is smaller than a first threshold level on a minus side or larger than a second threshold level on a plus side;

second ocular movement detecting means, having a two-dimensional image pickup element for picking up an image of an anterior portion of the eye, for detecting a predetermined position of the anterior portion by processing the image picked up by the image pickup element;

moving means for relatively moving an irradiation position of the treatment laser beam with respect to the eye; and movement control means for controlling moving means based on a result of detection by the second ocular movement detecting means so that the irradiation position is moved if the detected position is located out of a first allowable range with respect to a reference position, wherein the irradiation control means controls the irradiating means based on the result of detection by the second ocular movement detecting means so that the irradiation of the treatment laser beam is enabled if the detected position is located within a second allowable range with respect to the referenced position.

8. The apparatus of claim 7, wherein the movement control means controls the moving means based on the result of detection by the first ocular movement detecting means.

* * * * *

UNITED STATES PATENT AND TRADEMARK OFFICE
CERTIFICATE OF CORRECTION

PATENT NO.    : 6,585,724 B2
DATED         : July 1, 2003
INVENTOR(S)   : Minoru Toh It is certified that error appears in the above-identified patent and that said Letters Patent is hereby corrected as shown below:

Column 10,
Line 65, "opthalmic" should read -- ophthalmic --.

Column 11,
Line 19, "of anterior" should read -- of an interior --.

Signed and Sealed this

Eleventh Day of November, 2003

JAMES E. ROGAN
*Director of the United States Patent and Trademark Office*